(12) United States Patent
Marczyk

(10) Patent No.: US 9,867,616 B2
(45) Date of Patent: Jan. 16, 2018

(54) VARIABLE COMPRESSION SURGICAL FASTENER CARTRIDGE

(71) Applicant: Covidien LP, Mansfield, MA (US)

(72) Inventor: Stanislaw Marczyk, Stratford, CT (US)

(73) Assignee: COVIDIEN LP, Mansfield, MA (US)

( * ) Notice: Subject to any disclaimer, the term of this patent is extended or adjusted under 35 U.S.C. 154(b) by 694 days.

(21) Appl. No.: 13/915,730

(22) Filed: Jun. 12, 2013

(65) Prior Publication Data

US 2013/0270323 A1 Oct. 17, 2013

Related U.S. Application Data

(63) Continuation of application No. 12/410,850, filed on Mar. 25, 2009, now Pat. No. 8,464,922.

(60) Provisional application No. 61/051,890, filed on May 9, 2008.

(51) Int. Cl.
*A61B 17/072* (2006.01)
*A61B 17/064* (2006.01)

(52) U.S. Cl.
CPC .... *A61B 17/07207* (2013.01); *A61B 17/0644* (2013.01); *A61B 2017/07242* (2013.01); *A61B 2017/07271* (2013.01); *A61B 2017/07278* (2013.01)

(58) Field of Classification Search
CPC .... A61B 2017/00862; A61B 2017/068; A61B 2017/07278
USPC ...................................................... 227/175.1
See application file for complete search history.

(56) References Cited

U.S. PATENT DOCUMENTS

| | | | |
|---|---|---|---|
| 1,756,670 | A | 8/1926 | Treat |
| 3,079,606 | A | 3/1963 | Bobrov et al. |
| 3,258,012 | A | 6/1966 | Nakayama et al. |
| 3,744,495 | A | 7/1973 | Johnson |
| 3,771,526 | A | 11/1973 | Rudie |
| 3,807,394 | A | 4/1974 | Attenborough |

(Continued)

FOREIGN PATENT DOCUMENTS

| | | |
|---|---|---|
| EP | 0129442 | 12/1984 |
| EP | 0169044 | 1/1986 |

(Continued)

OTHER PUBLICATIONS

European Examination Report in European Patent Application No. EP 09 251 793.7, dated Sep. 20, 2010.

(Continued)

*Primary Examiner* — Thanh Truong
*Assistant Examiner* — Patrick Fry

(57) ABSTRACT

A surgical fastener cartridge is provided and includes a cartridge body having a tissue contacting surface that includes a plurality of fastener retention slots. A plurality of surgical fasteners is operatively disposed in the plurality of fastener retention slots. A plurality of pushers is operably associated with the plurality of surgical fasteners. Each pusher is configured for ejecting an associated surgical fastener towards a depression in an anvil. An actuation sled is housed within the cartridge body and includes a plurality of cam wedges. The plurality of cam wedges configured to sequentially contact the plurality of pushers such that a surgical fastener that is ejected closer to a cut line produces a greater compression force to stapled tissue than a surgical fastener ejected further from the cut line.

15 Claims, 11 Drawing Sheets

(56) References Cited

U.S. PATENT DOCUMENTS

| | | | |
|---|---|---|---|
| 3,837,555 A | 9/1974 | Green | |
| 4,014,492 A | 3/1977 | Rothfuss | |
| 4,278,091 A | 7/1981 | Borzone | |
| 4,319,576 A | 3/1982 | Rothfuss | |
| 4,475,679 A | 10/1984 | Fleury, Jr. | |
| 4,527,437 A | 7/1985 | Wells | |
| 4,531,522 A | 7/1985 | Bedi et al. | |
| 4,532,927 A | 8/1985 | Miksza, Jr. | |
| 4,548,202 A | 10/1985 | Duncan | |
| 4,573,469 A | 3/1986 | Golden et al. | |
| 4,605,001 A | 8/1986 | Rothfuss et al. | |
| 4,608,981 A | 9/1986 | Rothfuss et al. | |
| 4,610,383 A | 9/1986 | Rothfuss et al. | |
| 4,627,437 A | 12/1986 | Bedi et al. | |
| 4,723,540 A | 2/1988 | Gilmer, Jr. | |
| 4,741,336 A | 5/1988 | Failla et al. | |
| 4,767,044 A | 8/1988 | Green | |
| 4,809,695 A | 3/1989 | Gwathmey et al. | |
| 4,848,637 A | 7/1989 | Pruitt | |
| 4,881,545 A | 11/1989 | Isaacs et al. | |
| 4,930,503 A | 6/1990 | Pruitt | |
| 4,941,623 A | 7/1990 | Pruitt | |
| 4,978,049 A | 12/1990 | Green | |
| 5,027,834 A | 7/1991 | Pruitt | |
| 5,108,422 A | 4/1992 | Green et al. | |
| 5,180,092 A | 1/1993 | Crainich | |
| 5,201,746 A | 4/1993 | Shichman | |
| 5,209,756 A | 5/1993 | Seedhom et al. | |
| 5,219,353 A | 6/1993 | Garvey, III et al. | |
| 5,240,163 A | 8/1993 | Stein et al. | |
| 5,282,829 A | 2/1994 | Hermes | |
| 5,318,221 A | 6/1994 | Green et al. | |
| 5,342,396 A | 8/1994 | Cook | |
| 5,350,400 A | 9/1994 | Esposito et al. | |
| 5,352,229 A | 10/1994 | Goble et al. | |
| 5,389,098 A * | 2/1995 | Tsuruta | A61B 17/00234 606/142 |
| 5,425,489 A | 6/1995 | Shichman et al. | |
| 5,439,479 A | 8/1995 | Shichman et al. | |
| 5,441,193 A | 8/1995 | Gravener | |
| 5,452,836 A | 9/1995 | Huitema et al. | |
| 5,452,837 A | 9/1995 | Williamson, IV et al. | |
| 5,470,010 A | 11/1995 | Rothfuss et al. | |
| 5,484,095 A | 1/1996 | Green et al. | |
| 5,497,931 A | 3/1996 | Nakamura | |
| 5,501,693 A | 3/1996 | Gravener | |
| 5,507,426 A | 4/1996 | Young et al. | |
| 5,509,920 A | 4/1996 | Phillips et al. | |
| 5,571,116 A | 11/1996 | Bolanos | |
| 5,571,285 A | 11/1996 | Chow et al. | |
| 5,584,856 A | 12/1996 | Jameel et al. | |
| 5,620,452 A | 4/1997 | Yoon | |
| 5,632,432 A * | 5/1997 | Schulze | A61B 17/07207 227/176.1 |
| 5,634,926 A | 6/1997 | Jobe | |
| 5,667,526 A | 9/1997 | Levin | |
| 5,667,527 A | 9/1997 | Cook | |
| 5,676,674 A | 10/1997 | Bolanos et al. | |
| 5,697,542 A | 12/1997 | Knodel et al. | |
| 5,709,680 A | 1/1998 | Yates et al. | |
| 5,741,268 A | 4/1998 | Schutz | |
| 5,779,130 A | 7/1998 | Alesi et al. | |
| 5,782,396 A | 7/1998 | Mastri et al. | |
| 5,797,538 A | 8/1998 | Heaton et al. | |
| 5,810,822 A | 9/1998 | Mortier | |
| 5,817,109 A | 10/1998 | McGarry et al. | |
| 5,836,503 A | 11/1998 | Ehrenfels et al. | |
| 5,862,972 A | 1/1999 | Green et al. | |
| 5,865,361 A | 2/1999 | Milliman et al. | |
| 5,871,135 A | 2/1999 | Williamson, IV et al. | |
| 5,878,937 A | 3/1999 | Green et al. | |
| 5,879,371 A | 3/1999 | Gardiner et al. | |
| 5,894,979 A | 4/1999 | Powell | |
| 5,915,616 A | 6/1999 | Viola et al. | |
| 5,961,521 A | 10/1999 | Roger | |
| 5,964,394 A | 10/1999 | Robertson | |
| 6,045,560 A | 4/2000 | McKean et al. | |
| 6,083,242 A | 7/2000 | Cook | |
| 6,202,914 B1 | 3/2001 | Geiste et al. | |
| 6,273,897 B1 | 8/2001 | Dalessandro et al. | |
| 6,325,810 B1 | 12/2001 | Hamilton et al. | |
| 6,348,054 B1 | 2/2002 | Allen | |
| 6,485,493 B1 | 11/2002 | Bremer | |
| 6,702,826 B2 | 3/2004 | Liddicoat et al. | |
| 6,706,057 B1 | 3/2004 | Bidoia et al. | |
| 6,786,382 B1 | 9/2004 | Hoffman | |
| 6,905,057 B2 | 6/2005 | Swayze et al. | |
| 6,959,852 B2 | 11/2005 | Shelton, IV et al. | |
| 6,964,363 B2 | 11/2005 | Wales et al. | |
| 6,978,921 B2 | 12/2005 | Shelton, IV et al. | |
| 6,978,922 B2 | 12/2005 | Bilotti et al. | |
| 6,988,649 B2 | 1/2006 | Shelton, IV et al. | |
| 7,000,818 B2 | 2/2006 | Shelton, IV et al. | |
| 7,000,819 B2 | 2/2006 | Swayze et al. | |
| 7,001,411 B1 | 2/2006 | Dean | |
| 7,044,352 B2 | 5/2006 | Shelton, IV et al. | |
| 7,055,731 B2 | 6/2006 | Shelton, IV et al. | |
| 7,059,508 B2 | 6/2006 | Shelton, IV et al. | |
| 7,070,083 B2 | 7/2006 | Jankowski | |
| 7,147,140 B2 | 12/2006 | Wukusick et al. | |
| 7,258,262 B2 | 8/2007 | Mastri et al. | |
| 7,377,928 B2 | 5/2008 | Zubik et al. | |
| 7,398,907 B2 | 7/2008 | Racenet et al. | |
| 7,398,908 B2 | 7/2008 | Holsten et al. | |
| 7,401,721 B2 | 7/2008 | Holsten et al. | |
| 7,407,076 B2 | 8/2008 | Racenet et al. | |
| 7,455,676 B2 | 11/2008 | Holsten et al. | |
| 7,472,815 B2 | 1/2009 | Shelton et al. | |
| 7,500,979 B2 | 3/2009 | Hueil et al. | |
| 7,506,791 B2 | 3/2009 | Omaits et al. | |
| 7,547,312 B2 | 6/2009 | Bauman et al. | |
| 7,604,151 B2 | 10/2009 | Hess et al. | |
| 7,641,091 B2 | 1/2010 | Olson et al. | |
| 7,669,746 B2 | 3/2010 | Shelton | |
| 7,722,610 B2 | 5/2010 | Viola et al. | |
| 7,794,475 B2 | 9/2010 | Hess et al. | |
| 7,926,691 B2 | 4/2011 | Viola et al. | |
| 8,231,040 B2 | 7/2012 | Zemlok et al. | |
| 8,573,461 B2 * | 11/2013 | Shelton, IV | A61B 17/07207 227/175.1 |
| 9,038,881 B1 * | 5/2015 | Schaller | A61B 17/064 227/176.1 |
| 2002/0042621 A1 | 4/2002 | Liddicoat et al. | |
| 2004/0004105 A1 | 1/2004 | Jankowski | |
| 2004/0073222 A1 | 4/2004 | Koseki | |
| 2004/0232195 A1 | 11/2004 | Shelton et al. | |
| 2004/0232199 A1 | 11/2004 | Shelton et al. | |
| 2004/0247415 A1 | 12/2004 | Mangone, Jr. | |
| 2005/0006430 A1 | 1/2005 | Wales | |
| 2005/0006431 A1 | 1/2005 | Shelton et al. | |
| 2005/0006434 A1 | 1/2005 | Wales | |
| 2005/0023324 A1 | 2/2005 | Doll et al. | |
| 2005/0023325 A1 | 2/2005 | Gresham et al. | |
| 2005/0070925 A1 | 3/2005 | Shelton, IV et al. | |
| 2005/0070958 A1 | 3/2005 | Swayze et al. | |
| 2005/0173490 A1 | 8/2005 | Shelton, IV | |
| 2005/0178813 A1 | 8/2005 | Swayze et al. | |
| 2005/0187576 A1 | 8/2005 | Whitman et al. | |
| 2005/0263562 A1 | 12/2005 | Shelton, IV et al. | |
| 2005/0267530 A1 | 12/2005 | Cummins | |
| 2006/0000868 A1 | 1/2006 | Shelton, IV et al. | |
| 2006/0015144 A1 | 1/2006 | Burbank et al. | |
| 2006/0022014 A1 | 2/2006 | Shelton, IV et al. | |
| 2006/0022015 A1 | 2/2006 | Shelton, IV et al. | |
| 2006/0025809 A1 | 2/2006 | Shelton, IV | |
| 2006/0025810 A1 | 2/2006 | Shelton, IV | |
| 2006/0025811 A1 | 2/2006 | Shelton, IV | |
| 2006/0025812 A1 | 2/2006 | Shelton, IV | |
| 2006/0025813 A1 | 2/2006 | Shelton, IV et al. | |
| 2006/0025816 A1 | 2/2006 | Shelton, IV | |
| 2006/0025817 A1 | 2/2006 | Ortiz et al. | |
| 2006/0039779 A1 | 2/2006 | Ring | |
| 2006/0049230 A1 | 3/2006 | Shelton, IV et al. | |
| 2006/0085030 A1 | 4/2006 | Bettuchi et al. | |

(56) References Cited

U.S. PATENT DOCUMENTS

| | | |
|---|---|---|
| 2006/0097026 A1 | 5/2006 | Shelton, IV |
| 2006/0124688 A1 | 6/2006 | Racenet et al. |
| 2006/0163312 A1 | 7/2006 | Viola et al. |
| 2006/0226196 A1 | 10/2006 | Hueil et al. |
| 2006/0291981 A1 | 12/2006 | Viola et al. |
| 2007/0010838 A1 | 1/2007 | Shelton, IV et al. |
| 2007/0075115 A1 | 4/2007 | Olson et al. |
| 2007/0131732 A1 | 6/2007 | Holsten et al. |
| 2007/0244351 A1 | 10/2007 | Wazer et al. |
| 2007/0262116 A1 | 11/2007 | Hueil et al. |
| 2008/0041918 A1 | 2/2008 | Holsten et al. |
| 2008/0078800 A1 | 4/2008 | Hess et al. |
| 2008/0078803 A1 | 4/2008 | Shelton et al. |
| 2008/0078804 A1 | 4/2008 | Shelton et al. |
| 2011/0168760 A1 | 7/2011 | Viola et al. |

FOREIGN PATENT DOCUMENTS

| | | |
|---|---|---|
| EP | 0588081 | 3/1994 |
| EP | 0878169 | 11/1998 |
| EP | 0640315 | 12/1998 |
| EP | 1090592 | 4/2001 |
| EP | 1316290 | 6/2003 |
| EP | 1479346 | 11/2004 |
| EP | 1607048 | 12/2005 |
| EP | 1785098 | 8/2006 |
| EP | 1728473 | 12/2006 |
| EP | 1754445 | 2/2007 |
| EP | 1785098 | 3/2007 |
| EP | 1875868 | 1/2008 |
| EP | 2095777 | 9/2009 |
| EP | 2110083 A2 | 10/2009 |
| FR | 2838952 | 10/2003 |
| GB | 1299336 | 12/1972 |
| GB | 2019296 | 10/1979 |
| GB | 2029754 | 3/1980 |
| GB | 2051287 | 1/1981 |
| SU | 405234 | 9/1975 |
| SU | 1333319 | 8/1987 |
| SU | 1442191 | 12/1988 |
| SU | 1459659 | 2/1989 |
| WO | WO 86/02254 | 4/1986 |
| WO | WO 90/05489 | 5/1990 |
| WO | WO 96/19146 | 6/1996 |
| WO | WO 97/34533 | 9/1997 |
| WO | WO 02/30296 | 4/2002 |
| WO | WO 03/094743 | 11/2003 |
| WO | WO 03/094747 | 11/2003 |
| WO | WO 2006/055385 | 5/2006 |
| WO | WO 2008/003371 | 1/2008 |
| WO | WO 2008/007377 | 1/2008 |
| WO | WO 2008/039249 | 4/2008 |
| WO | WO2008/039250 | 4/2008 |
| WO | WO 2008/039250 | 4/2008 |
| WO | WO 2008/089050 | 7/2008 |

OTHER PUBLICATIONS

European Search Report EP 10251797 dated Jan. 31, 2011.
European Search Report EP 07254366 dated Nov. 11, 2010.
European Search Report EP 09251067 dated Mar. 17, 2011.
European Search Report EP 06016963 dated Mar. 9, 2007.
European Search Report EP 08252283 dated Jan. 15, 2009.
European Search Report EP 09251224 dated Oct. 8, 2009.
European Search Report EP 09251240 dated Oct. 19, 2009.
European Search Report EP 09251268 dated Sep. 25, 2009.
European Search Report EP 09251793 dated Nov. 16, 2009.
European Search Report EP 11004299 dated Aug. 12, 2011.
European Search Report EP 09251067 dated Mar. 9, 2011.
European Search Report EP 09251276 completed Apr. 13, 2012.
European Search Report EP 09251269 dated May 27, 2013.
European Search Report EP 15151525 dated May 7, 2015.
European Search Report dated Feb. 1, 2017 in EP Application No. 16186617.3.

* cited by examiner

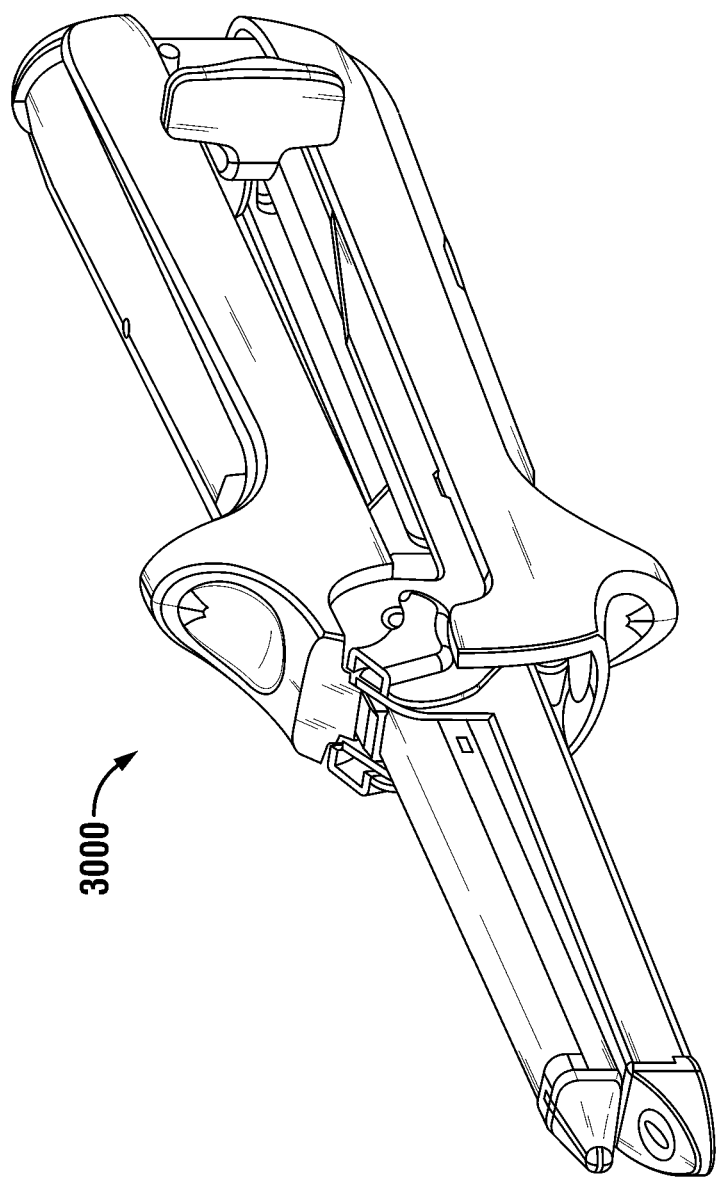

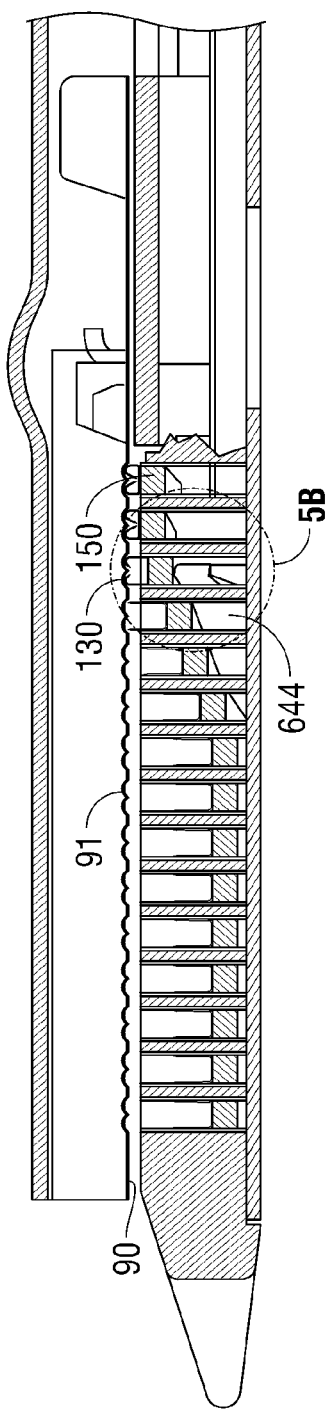
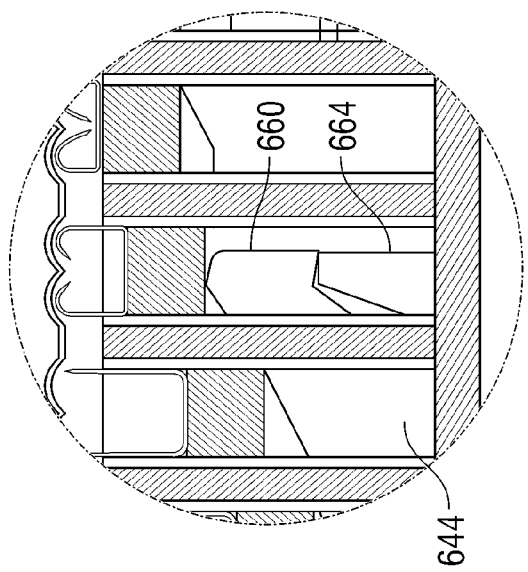
FIG. 5A
FIG. 5B

VARIABLE COMPRESSION SURGICAL FASTENER CARTRIDGE

CROSS-REFERENCE TO RELATED APPLICATIONS

This application is a continuation of U.S. application Ser. No. 12/410,850 filed Mar. 25, 2009, which claims benefit of Provisional application No. 61/051,890 filed May 9, 2008, and the disclosures of each of the above-identified applications are hereby incorporated by reference in their entirety.

BACKGROUND

1. Technical Field

The present disclosure relates to surgical fastener applying apparatus. More particularly, the present disclosure relates to a surgical fastener cartridge that includes a plurality of surgical fasteners and a mechanism for forming the surgical fasteners so as to apply different compressive forces to tissue depending on the location of the tissue with respect to the cartridge, and methods of manufacturing and using the same.

2. Background of the Related Art

Commercially available surgical fastening apparatus are well known in the art, some of which are specifically adapted for use in various surgical procedures including, but not limited to, end-to-end anastomosis, circular end-to-end anastomosis, open gastrointestinal anastomosis, endoscopic gastrointestinal anastomosis, and transverse anastomosis. U.S. Pat. Nos. 5,915,616; 6,202,914; 5,865,361; and 5,964,394 each describe one or more suitable apparatus which may be employed while performing one of these procedures.

In general, a surgical fastening apparatus will include an anvil that is approximated relative to a fastener cartridge during use. The anvil includes depressions that are aligned with, and/or are in registration with slots defined in the cartridge, through which the fasteners will emerge. To effectuate formation, the fasteners emerge from the cartridge and are driven against the anvil. The fastener cartridge typically has one or more rows of fasteners disposed alongside a channel that is configured to accommodate a knife, or other such cutting element, such that tissue can be simultaneously cut and joined together. Depending upon the particular surgical fastening apparatus, the rows of fasteners may be arranged in a linear or non-linear, e.g. circular, semi-circular, or otherwise arcuate configuration.

Various types of surgical fasteners are well known in the art, including but not limited to unitary fasteners and two-part fasteners. Unitary fasteners have a pre-formed configuration and a formed configuration. Unitary fasteners generally include a pair of legs adapted to penetrate tissue and connected by a backspan from which they extend. In use, subsequent to formation, certain types of the unitary fasteners have a "B" shaped configuration. Typically, the two-part fastener includes legs that are barbed and connected by a backspan which are engaged and locked into a separate retainer piece that is usually located in the anvil. In use, the two-part fastener is pressed into the tissue so that the barbs penetrate the tissue and emerge from the other side where they are then locked into the retainer piece. The retainers prevent the two-part fastener from dislodging from the tissue. The two-part fasteners are not intended to be unlocked or removable. They are generally made of a bioabsorbable material.

A common concern in each of these procedures is hemostasis, or the rate at which bleeding of the target tissue is stopped. It is commonly known that by increasing the amount of pressure applied to a wound, the flow of blood can be limited, thereby decreasing the time necessary to achieve hemostasis. To this end, conventional surgical fastening apparatus generally apply two or more rows of fasteners about the cut-line to compress the surrounding tissue in an effort to stop any bleeding and to join the cut tissue together. Each of the fasteners will generally apply a compressive force to the tissue sufficient to effectuate hemostasis, however, if too much pressure is applied, this can result in a needless reduction in blood flow to the tissue surrounding the cut-line. Accordingly, the joining of tissue together in this manner may result in an elevated level of necrosis, a slower rate of healing, and/or a greater convalescence.

Consequently, it would be advantageous to provide a surgical fastening apparatus capable of limiting the flow of blood in the tissue immediately adjacent the cut tissue to effectuate hemostasis and wound closure, while maximizing blood flow in the surrounding tissue to facilitate healing. Additionally, when tissue is clamped and compressed between the anvil and cartridge, some of the fluid of the tissue is squeezed out so the tissue is compressed further at the portions of the cartridge adjacent the cut-line and anvil than at the lateral edges it may also be desirable to cut and staple across tissue that varies in thickness. It would therefore be advantageous to provide staples which could better accommodate these resulting different tissue thicknesses.

SUMMARY

The present disclosure provides a surgical fastener cartridge. The surgical fastener cartridge includes a cartridge body having a tissue contacting surface that includes a plurality of fastener retention slots. In certain embodiments, the tissue contacting surface includes a channel configured to accommodate longitudinal movement of a cutting element. A plurality of surgical fasteners is operatively disposed in the plurality of fastener retention slots. A plurality of pushers is operably associated with the plurality of surgical fasteners. In an embodiment, each pusher is configured for ejecting an associated surgical fastener towards a depression in an anvil. An actuation sled is housed within the cartridge body and includes a plurality of cam wedges disposed on opposing sides of a central support associated with the actuation sled. The plurality of cam wedges is configured to sequentially contact the plurality of pushers such that a surgical fastener that is ejected closer to a cut line produces a greater compression force to stapled tissue than a surgical fastener ejected further from the cut line such that a desired hemostatic effect is achieved. In certain embodiments, the surgical fastener cartridge has a sled with a first cam wedge having a proximal end and a second cam wedge having a proximal end, the proximal end of the first cam wedge including a notched area configured to deflect the proximal end of the first cam wedge during the formation of the surgical fasteners In embodiments, the actuation sled is adapted to operatively connect to a drive assembly associated with a surgical fastening apparatus such that the actuation sled is longitudinally movable within the cartridge body.

In certain embodiments, a central support of the sled is configured to engage an abutment surface of the cutting element.

In embodiments, the plurality of cam wedges on opposing sides of the central support includes inner, middle, and outer cam wedges. The inner cam wedges may include proximal ends that are relatively rigid and the middle and outer cam wedges each include proximal ends that are relatively flexible. In embodiments, the middle and outer cam wedges each define a respective gap distance "$G_1$" and "$G_2$". In embodiments, each of the gap distances "$G_1$", "$G_2$" separate respective deflectable portions of middle and outer cam wedges, wherein the respective deflectable portions are configured to deflect toward a base of the actuation sled when the plurality of surgical fastener contacts a corresponding surgical fastener forming depression associated with an anvil of the surgical fastening apparatus. In embodiments, the gap distance "$G_1$" of the middle cam wedge may be less than the gap distance "$G_2$" of the outer cam wedge. The deflectable portions may be configured to contact a respective non-deflectable portion of the middle and outer cam wedges.

In certain embodiments, each of the proximal ends of middle and outer cam wedges include a notched area configured to alter the amount of deflection of the middle and outer cam wedges.

BRIEF DESCRIPTION OF THE DRAWINGS

Various embodiments of the present disclosure are described hereinbelow with references to the drawings, wherein:

FIG. 3 illustrates another type of surgical fastener instrument that may employ an alternate embodiment of surgical fastener cartridge in accordance with the present disclosure;

FIG. 5A is a partial cross-sectional view of the surgical fastener cartridge depicted in FIG. 4B;

FIG. 5B is an enlarged view of the area of detail represented by 5B depicted in FIG. 5A.

FIG. 6A-1 is a side perspective cutaway view taken along line segment $A_1$-$A_1$ of the surgical fastener depicted in FIG. 6A;

DETAILED DESCRIPTION OF EXEMPLARY EMBODIMENTS

Figure 1:
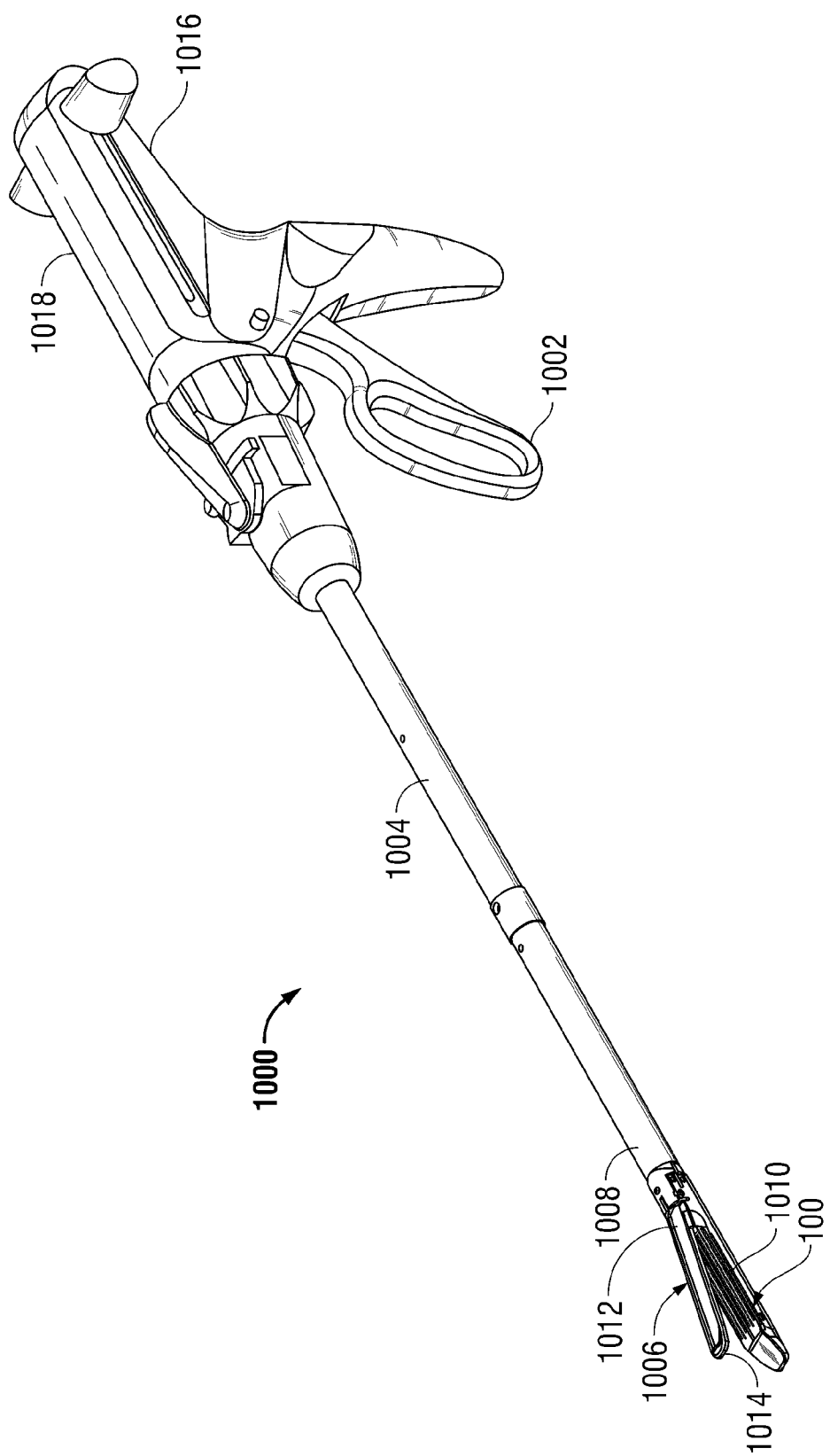
FIG. 1 illustrates a surgical fastener applying apparatus for use with a surgical fastener cartridge that employs surgical fasteners in accordance with embodiments of the present disclosure.

Various exemplary embodiments of the presently disclosed surgical fastener cartridge, and method of manufacturing the same, will now be described in detail with reference to the drawings wherein like references numerals identify similar or identical elements. In the drawings and in the description which follows, the term "proximal" will refer to the end of the surgical fastener cartridge that is closer to the operator during use, while the term "distal" will refer to the end of the fastener cartridge that is further from the operator, as is traditional and conventional in the art. In addition, the term "surgical fastener" should be understood to include any structure formed of a biocompatible material that is suitable for the intended purpose of joining tissue together, including but not being limited to surgical staples, clips, and the like.

The present disclosure provides a surgical fastener cartridge adapted to house a plurality of surgical fasteners and a mechanism for forming the surgical fasteners so as to apply different compressive forces to tissue depending on the location of the tissue with respect to the cartridge. Varying the degree of compression force can affect hemostasis of the tissue. To this end, in certain embodiments, the surgical fasteners are formed such that certain surgical fasteners produce a greater compression force to the tissue than other surgical fasteners deployed by the same cartridge.

With reference to FIG. 1, a surgical fastener applying apparatus 1000 that employs a surgical fastener cartridge 100 is illustrated. Surgical fastener applying apparatus 1000 is used to sequentially apply a plurality of surgical fasteners to a patient's tissue. Surgical fastener apparatus 1000 may be configured for use, subsequent sterilization and reuse, or may be configured for single use. Surgical fastener applying apparatus 1000 includes a housing 1016 that includes a barrel portion 1018, a movable handle 1002, an elongated shaft 1004 extending distally therefrom, and an operative tool 1006 coupled to a distal end 1008 of the elongated shaft 1004. In general, operative tool 1006 is adapted to clamp, sequentially fasten together, and sever adjacent tissue segments along a cut-line. Operative tool 1006 includes a pair of opposed jaws 1010, 1012 pivotally coupled with respect to one another and respectively including an anvil member 1014 and cartridge 100 that are approximated relative to one another during use. The anvil includes an anvil plate 90 having surgical fastener 130 forming depressions 91 that are aligned with, and/or are in registration with slots 126 (FIGS. 4A and 5A) defined in the cartridge 100. The fasteners 130 emerge through the slots 126, to be driven against anvil plate 90, as seen in FIG. 5A, for example. For a more detailed discussion of the approximation and firing of surgical fastener applying apparatus 1000, reference is made to commonly owned U.S. Pat. Nos. 7,258,262 and 5,865,361 currently assigned to Tyco Healthcare Group LP, the entire contents of which are incorporated herein by reference. The operative tool 1006 may comprise a removable and replaceable loading unit for the apparatus 1000. Alternatively, the cartridge 100 may comprise a removable and replaceable loading unit for the apparatus 1000.

Figure 2:
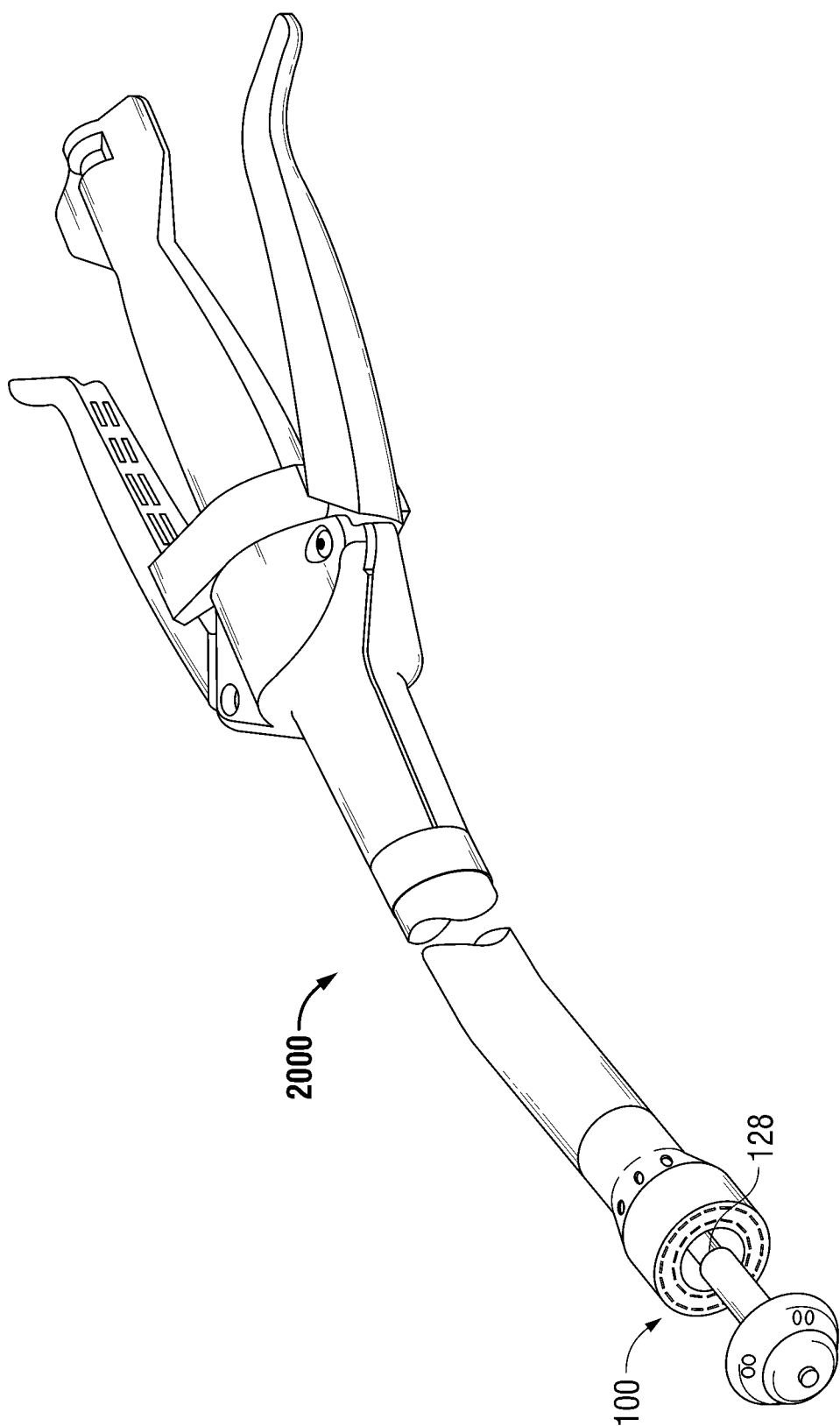
FIG. 2 illustrates another type of surgical fastener device that may employ an alternate embodiment of a surgical fastener cartridge in accordance with the present disclosure.

While surgical fastener applying apparatus 1000 is depicted as an apparatus suitable for use in laparoscopic procedures for performing surgical anastomotic fastening of tissue, those skilled in the art will appreciate that cartridge 100 may be adapted for use with any surgical instrument suitable for the intended purposes described herein. For example, cartridge 100 may be adapted for use with an end-to-end anastomosis device 2000, as seen in FIG. 2, and/or a surgical stapling instrument 3000, as seen in FIG. 3, for use during an open gastrointestinal anastomotic stapling procedure, or, for example, any of the surgical fastener applying apparatus discussed in U.S. Pat. Nos. 6,045,560; 5,964,394; 5,894,979; 5,878,937; 5,915,616; 5,836,503; 5,865,361; 5,862,972; 5,817,109; 5,797,538; and 5,782,396, which are each incorporated by reference herein in their entirety. The cartridge in certain embodiments is removable and replaceable with another loaded cartridge. In other embodiments, the operative tool 1006 is removable and replaceable.

For the purposes of brevity, the structural and operational features of cartridge 100 will be described in terms of use with the surgical fastener applying apparatus 1000.

Figure 4A:
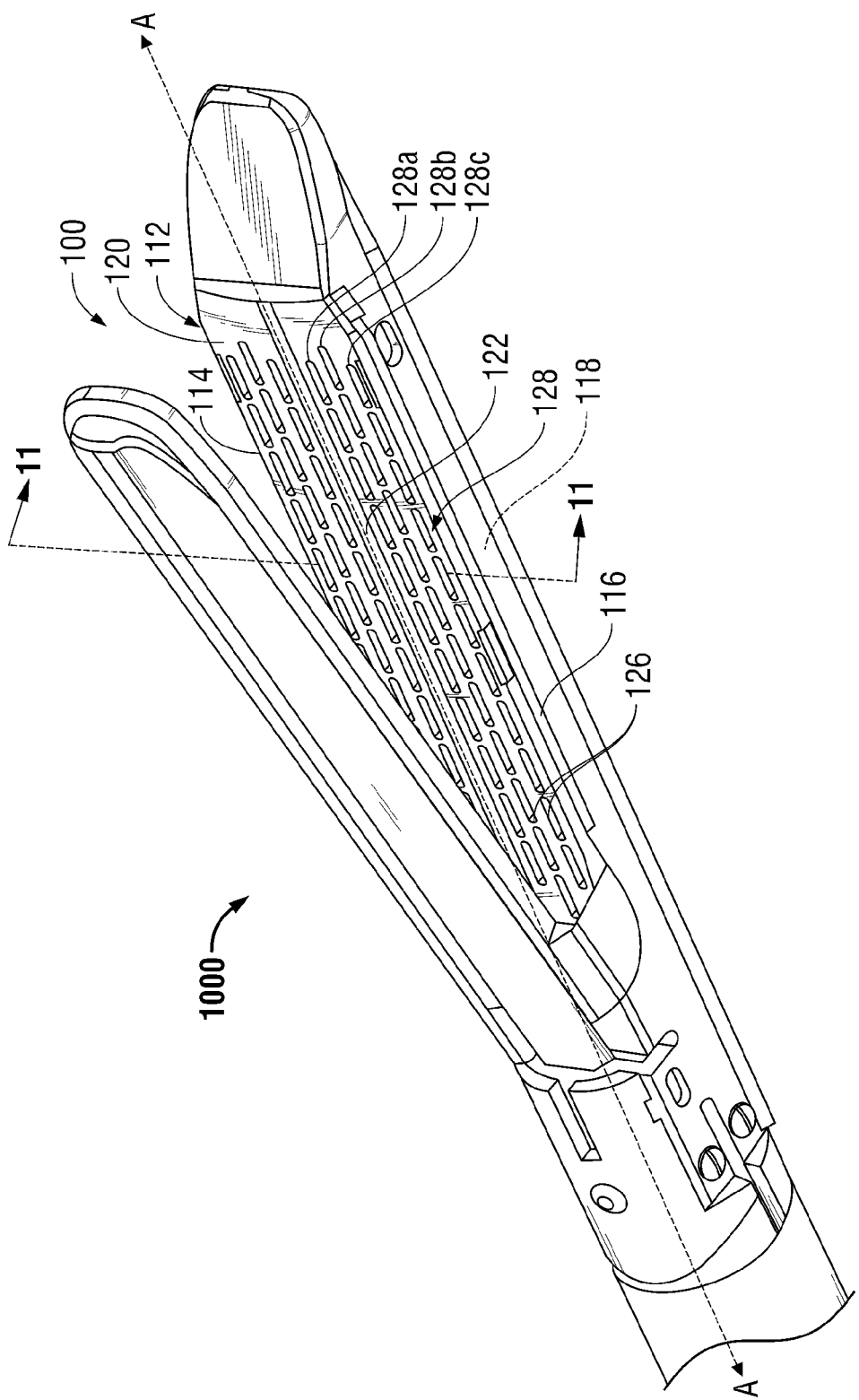
FIG. 4A is an enlarged top perspective view of the surgical fastener cartridge shown in FIG. 1.
Figure 4B:
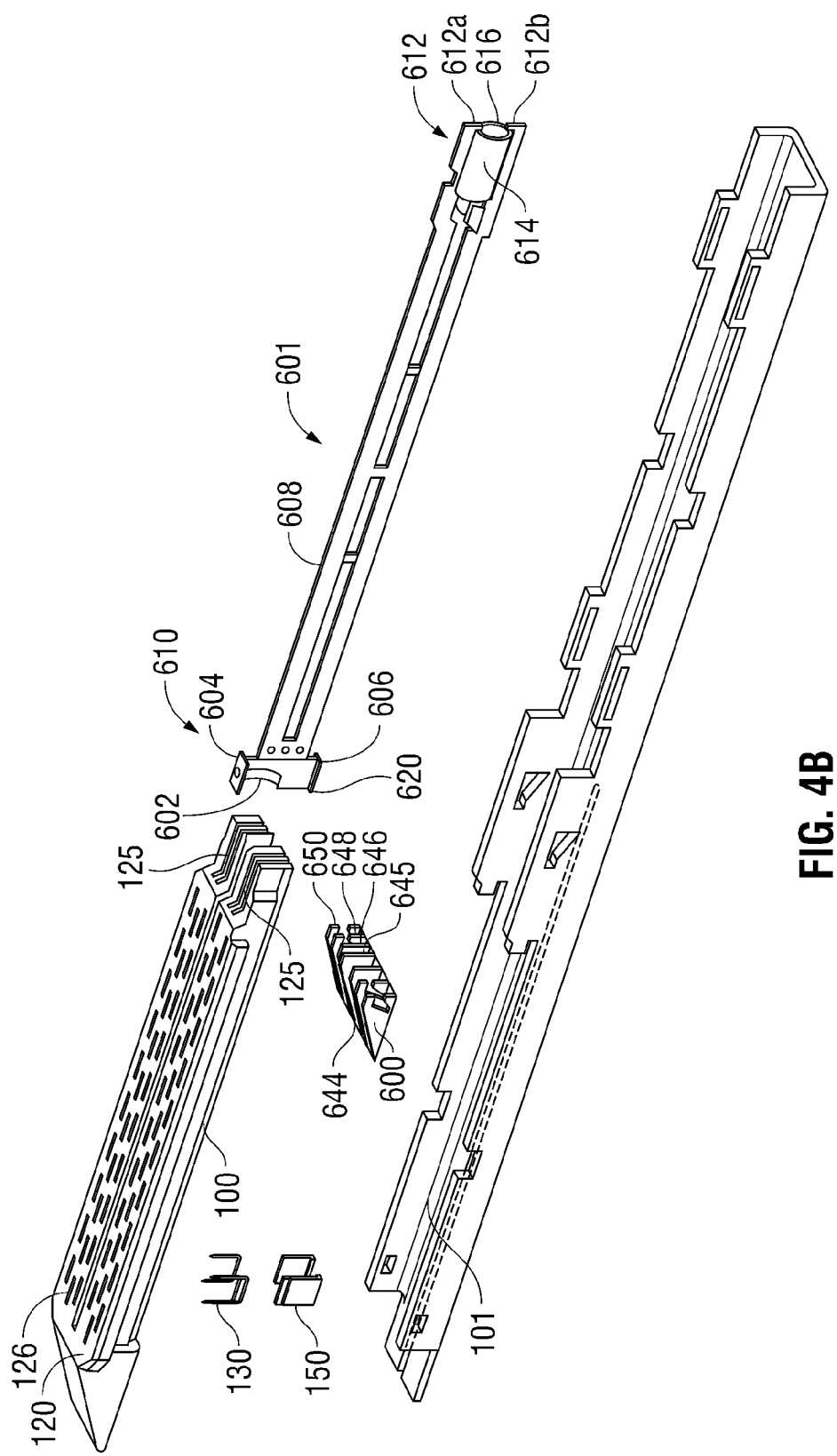
FIG. 4B is a partially exploded view of an alternate embodiment of a surgical fastener cartridge configured for use with the surgical fastener applying apparatus depicted in FIG. 3.

With reference to FIGS. 4A and 4B, and initially with reference to FIG. 4A, cartridge 100 is shown. Cartridge 100 extends along a longitudinal axis "A-A" and includes a cartridge body 112 with a pair of opposed side walls 114, 116, a bottom wall 118, and a tissue contacting surface 120. The tissue contacting surface 120 includes a channel 122 that is configured to accommodate longitudinal movement of a knife 602, or other suitable cutting element, such that stapled tissue may be severed along a cut-line. The cartridge also defines longitudinally extending recesses 125 that accommodate part of the surgical fastener forming mechanism and are discussed below. The tissue contacting surface 120 includes a plurality of fastener retention slots 126 that extend from the tissue contacting surface 120 into the cartridge and intersect with the longitudinally extending recesses 125. The fastener retention slots 126 are arranged in a plurality of rows 128 that extend substantially the length of the cartridge 100. As shown in FIG. 4A, the fastener retention slots 126 are arranged into a pair of first (inner) rows $128_A$ that are spaced laterally from the channel 122 and on opposite sides thereof, a pair of second (middle) rows $128_B$ that are spaced laterally from the pair of first rows $128_A$ and on opposite sides of the channel 122, and a pair of third (outer) rows $128_C$ that are spaced laterally from the pair of second rows $128_B$ and on opposite sides of channel 122. While the cartridge 100 is depicted as including pairs of first, second, and third rows $128_A$, $128_B$, $128_C$, respectively, it is within the purview of the present disclosure to have more or fewer rows of the fastener retention slots 126 disposed on cartridge 100. Additionally, rows 128 may be annular, as opposed to linear, and spaced radially from the cutting element; such is the case when the fastening cartridge is employed with the surgical fastening device depicted in FIG. 2.

Figure 11:
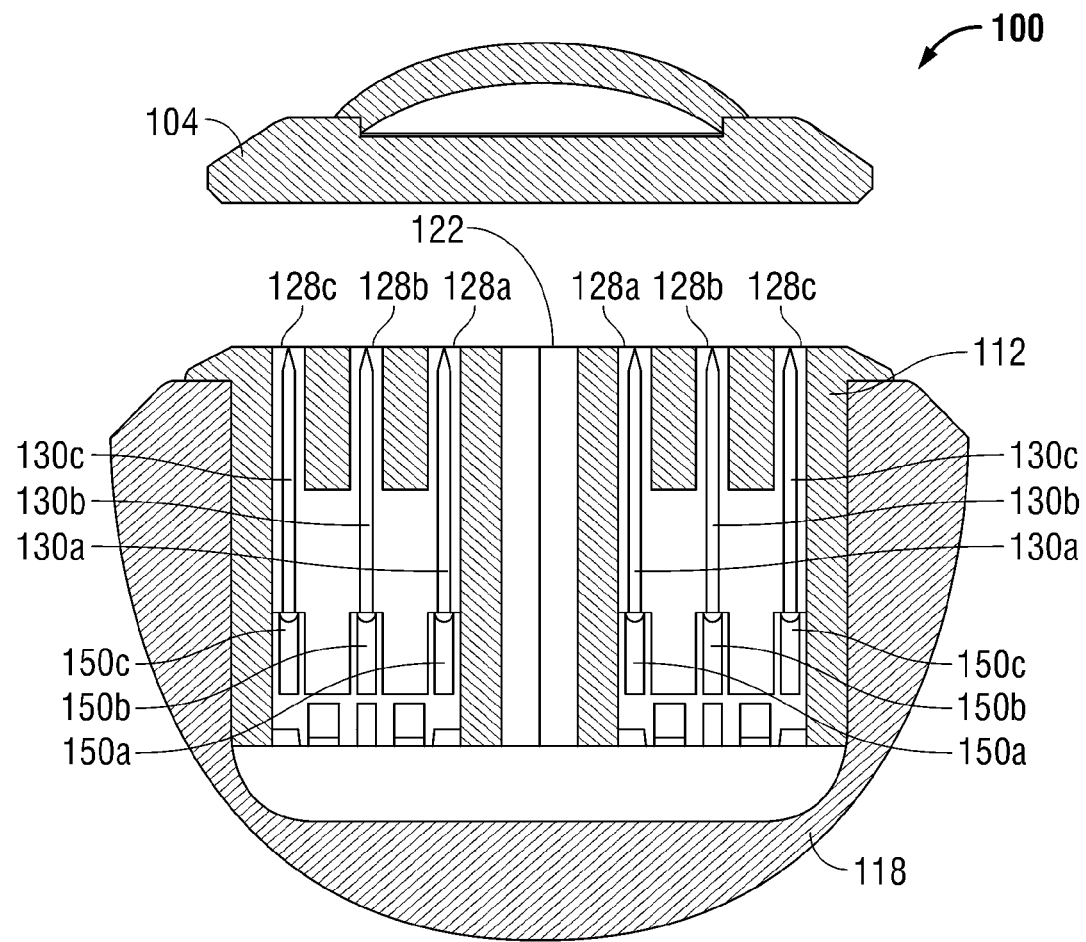
FIG. 11 is partial cross-sectional view taken along the line segment "9-9" in FIG. 4 illustrating the surgical fastener cartridge loaded with the surgical fasteners depicted in FIG. 6A.

With reference to FIG. 4B, each of the fastener retention slots 126 is configured to receive one of a plurality of surgical fasteners 130 and pushers 150 therein such that the surgical fasteners 130 are deployed in rows (e.g., inner, middle, and outer rows) on opposite sides of the cut-line created in the tissue during fastening, see FIG. 11 for example. Pushers 150 are at least partially disposed in the fastener retention slots 126 and are sequentially contacted by an actuation sled 600 which causes the staples 130 housed within staple cartridge 100 to be sequentially ejected therefrom (FIG. 5B).

The axial drive assembly 601 includes an elongated drive beam 608 including a distal working head 610 and a proximal engagement section 612. In an embodiment, drive beam 608 is constructed from multiple stacked sheets of material. Engagement section 612 includes a pair of resilient engagement fingers 612a and 612b which mountingly engage a pair of corresponding retention slots formed in a drive member 614. Drive member 614 includes a proximal porthole 616 configured to receive a stem at a distal end of a control rod (not shown) operably associated with the surgical fastener applying apparatus 1000. The control rod extends coaxially through the elongated body 1004 of surgical fastener applying apparatus 1000. The movable handle 1002 controls the linear movement of an actuation shaft (not shown) which is mounted within barrel portion 1016. More particularly, in embodiments the actuation shaft has a toothed rack defined thereon, and movable handle 1002 has a ratcheting pawl mounted thereto for incrementally engaging and advancing the actuation shaft. The pawl may be mounted on a pivot pin and a coiled torsion spring that biases the pawl into engagement with the toothed rack. In operation, when movable handle 1002 is pulled proximally, the pawl rotates counterclockwise and engages the teeth of the actuation shaft, thereby allowing movable handle 1002 to drive the shaft distally. An abutment surface 620 on the working head 610 is configured to engage a central support wedge 645 of actuation sled 600. Axial drive assembly 601, among other things, transmits the longitudinal drive forces exerted by the control rod disposed in elongated shaft 1004 to the actuation sled 600. For a more detailed description of the operative features of the axial drive assembly 601, movable handle 1002, actuation shaft, and control rod, reference is made to commonly owned U.S. Pat. No. 7,258,262, the contents of which are hereby incorporated by reference in its entirety.

The actuation sled 600 has an initial, proximal-most position. The working head 610 (of the axial drive assembly 601) is disposed in abutment with and proximal to the sled 600. The working head 610 has an upper flange 604 that engages the anvil member 1014 and a lower flange 606 that engages a channel 101 that supports the cartridge 100. The operative tool 1006 is first actuated to clamp onto tissue. Proximal movement of the movable handle 1002 advances the control rod distally. The control rod advances the axial drive assembly 601 so that the upper and lower flanges, 604 and 606, respectively, of the working head 610 engage the anvil member 1014 and channel 101, respectively, to approximate the anvil member 1014 and cartridge 100 with one another. With tissue clamped between anvil member 1014 and cartridge 100, the fasteners are fired from the apparatus into the tissue. The fasteners are fired by operating the handle 1002 again to further advance the knife 602 of working head 610. Accordingly, as illustrated in FIG. 5A, the axial drive assembly 601 drives actuation sled 600 distally into and through cartridge 100. During its distal translation, the actuation sled 600, and operative members associated therewith, travels through the longitudinally extending recesses 125 of the cartridge. Angled leading surfaces of the actuation sled 600 sequentially contact pushers 150 as the sled translates, contacting the pushers 150 at the shaped cam surfaces on the pushers 150. Through the interaction of the cam surfaces on the pushers and the angled leading surfaces of the actuation sled 600, the pushers 150 are urged in a direction transverse to the direction of movement of actuation sled 600. As a result, pushers 150 push surgical fasteners 130 from their individual slots 126, driving each surgical fastener 150 into a respective staple forming depression 91 of anvil plate 90. Sequential firing of the staples continues until actuation sled 600 is advanced to the distal end of cartridge 100, at which time, all of the staples once housed within cartridge 100 will have been ejected A more detailed description of the interaction between actuation sled 600 and pushers 150 will be described below.

Figures 1, 6A:
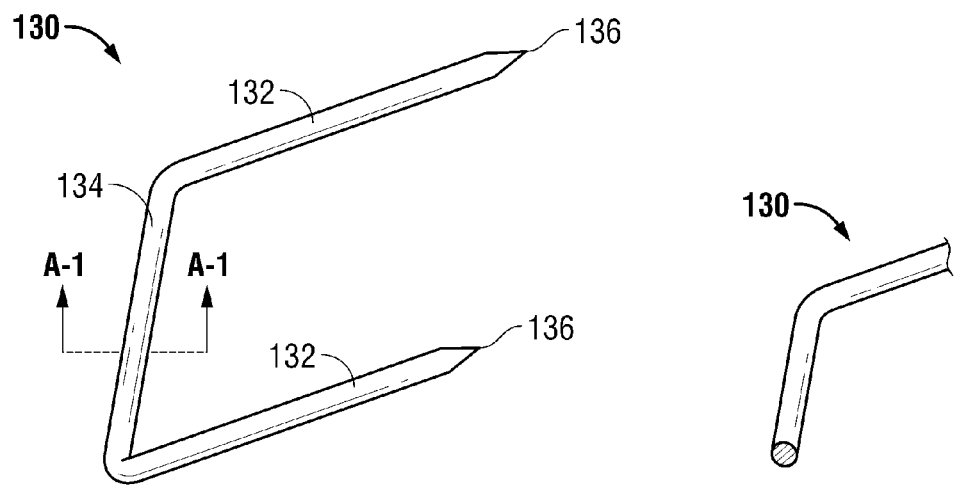
FIG. 6A is a side perspective view of a surgical fastener configured for use with the cartridge depicted in FIG. 4A prior to formation.

With reference now to FIGS. 6A, $6_{A-1}$, and 7A-7D, cartridge 100 may loaded with surgical fasteners, represented generally as surgical fastener 130. Surgical fastener 130 includes two legs 132 connected by a backspan 134 extending therebetween. The thickness of the backspan 134 and the legs 132 may be varied to fasten adjacent tissue segments "$T_1$", "$T_2$" of varying thickness. For a more detailed discussion of surgical fasteners that include backspans and legs that vary, reference is made to commonly owned U.S. Provisional Patent Application Nos. 61/044,682 and 61/044,664 currently assigned to Tyco Healthcare Group LP, the entire contents of which are incorporated herein by reference.

The legs 132 and the backspan 134 may define a cross-section having any suitable geometric configuration, including but not limited to rectangular, oval, square, triangular, and trapezoidal. The legs 132 and the backspan 134 may exhibit the same geometrical configuration such that the cross-sectional configuration of the surgical fastener 130 is substantially uniform, as shown in FIG. 6A, or, alternatively, the legs 132 and the backspan 134 may exhibit different geometrical configurations, e.g., the legs 132 may exhibit a rectangular cross-section and the backspan 34 may exhibit an oval cross-section, as shown in FIGS. 7A-7D. Backspan 134 and/or legs 132 may be formed by any suitable means known in the art including but not limited to welding, braising, coining, casting, overmolding and so on. Additionally, backspan 134 and/or legs 132 may be treated by way of annealing, cold working, heat treating, and so on. This may provide increased burst strength to the surgical fastener. Moreover, backspan may include different configurations of blocking and/or retainer material, tube, sleeve, collar, and/or grommet.

As seen in FIG. 6A, prior to the formation of surgical fastener 130, legs 132 extend from the backspan 134 such that they are substantially parallel. Alternatively, the legs 132 may converge or diverge from the backspan. The present disclosure contemplates that the surgical fastener 130 may also be configured as a directionally biased staple, such as those described in commonly owned U.S. patent application Ser. No. 11/253,493, filed Oct. 17, 2005, the entire contents of which are incorporated by reference herein.

Each of the legs 132 terminates in a penetrating end 136 that is configured to penetrate tissue (tissue segments "$T_1$", "$T_2$" for example) and/or other suitable material (blocking and/or retainer material for example). The penetrating ends 136 of legs 132 can be tapered to facilitate the penetration of tissue segments "$T_1$", "$T_2$", or alternatively, the penetrating ends 136 may not include a taper. In various embodiments, penetrating ends 136 may define a conical or flat surface, as described in co-pending U.S. patent application Ser. No. 11/444,761, filed Apr. 13, 2003, the entire contents of which are incorporated by reference herein. In embodiments, one or both of legs 132 may be barbed. Having legs 132 configured in such a manner may facilitate maintaining the surgical fastener 130 in a fixed position within the tissue and/or blocking material.

Figure 8:
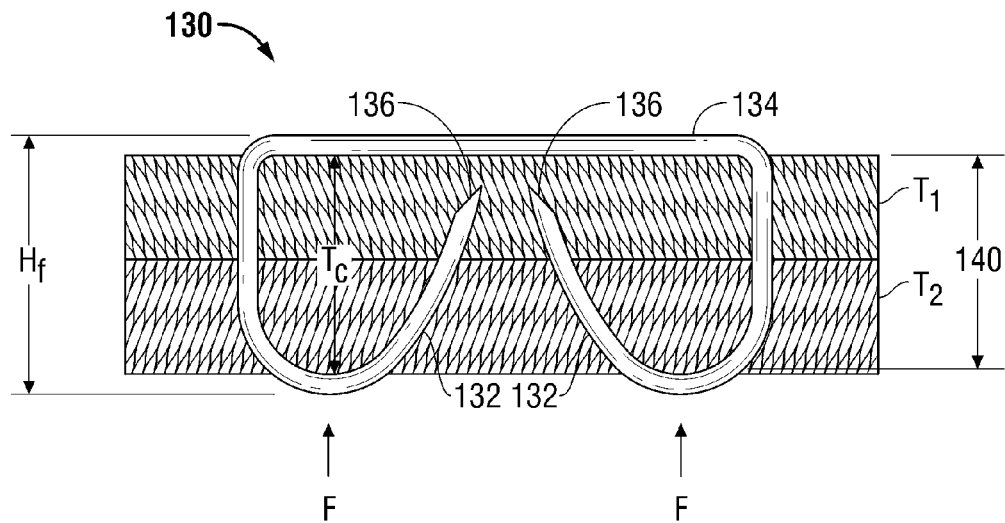
FIG. 8 is a side cross-sectional view of the surgical fastener depicted in FIG. 6A shown subsequent to formation and within adjacent tissue segments.

Turning now to FIG. 8, surgical fastener 130 is shown subsequent to formation. Surgical fastener 130 is configured to provide a compression force to stapled tissue occupied therein. To this end, legs 132 cooperate with backspan 134 to maintain adjacent tissue segments or layers "$T_1$", "$T_2$" in approximation and apply a compressive force "F" thereto. The compressive force "F" applies pressure to the tissue segments "$T_1$", "$T_2$", thereby restricting the flow of blood through the tissue surrounding the surgical fastener 130 and facilitating hemostasis. The amount of pressure that is applied to the tissue segments "$T_1$", "$T_2$" is limited such that the flow of blood through the tissue is not completely restricted. When formed, the surgical fastener 130 is generally "B" shaped with an overall height "$H_F$" (measured from the outermost surface of the backspan 134 to the outermost curve of the legs 132) and a tissue compression space 140.

Figure 9:
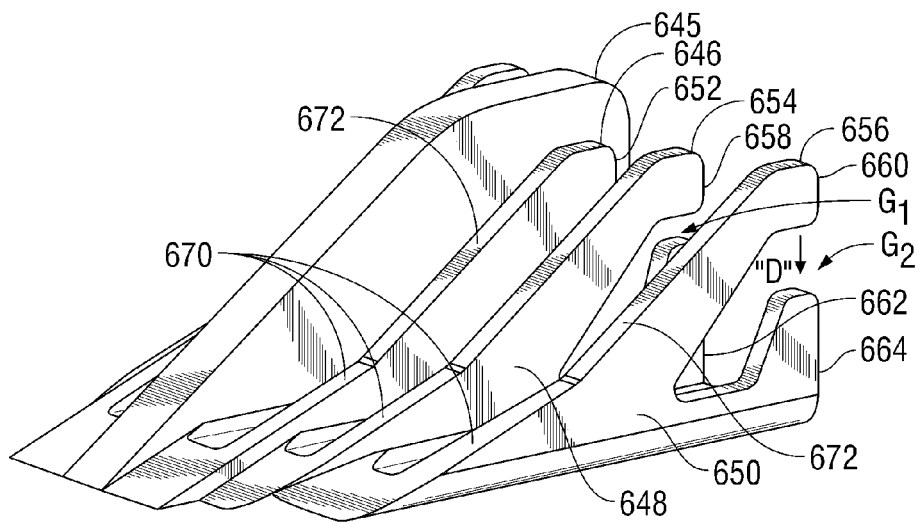
FIG. 9 is a side perspective view of a sled configuration depicted in FIG. 4B.

With reference to FIG. 9 sled 600 is shown. In certain embodiments disclosed herein, cartridge 100 is configured such that the surgical fastener 130 deployed closer to the cut-line or channel 122 provides a greater compression force to the stapled tissue than the surgical fastener 130 deployed further from the cut line. To this end, sled 600 includes one or more upstanding cam wedges 644 disposed on opposing sides of a central support 645, to correspond to the rows 128 of slots 126 provided in cartridge 100. Cam wedges 644 are receivable and movable within longitudinal recesses 125 when sled 600 is translated distally through cartridge 100. As noted above, sled 600 presents camming surfaces that contact and lift the pushers 150 upward, driving the surgical fasteners 130 up from the slots 126 into contact with surgical fastener 130 forming depressions 91, creating formed "B"-shaped staples, such as depicted in FIGS. 5B and 8. Central support 645 or portion thereof is configured to engage abutment surface 620 of axial drive assembly 601. Sled 600 is configured such that the cam wedges 644 driving the surgical fasteners 130 closer to the cut-line or channel 122 are relatively more rigid as compared to the cam wedges 644 driving the surgical fasteners further from the cut-line or channel 122, which are somewhat more flexible, deflectable, or collapsible. Essentially, the rigidity of the cam wedge 644 varies between a central region (i.e., more rigid) and an outer region (i.e., more flexible). Alternatively, reverse or other combinations and/or arrangements are contemplated. For example, in embodiments in which a channel 122 and knife bar 601 are not provided, one or more cam wedges 644 may be relatively flexible as compared to others. The cartridge may have one or more rows 128 of slots 126, wherein each of the one or more rows 128 includes a corresponding cam wedge 644.

In the embodiment shown, cam wedges 644 on each side of the central support 645 include inner, middle, and outer cam wedges, 646, 648, and 650, respectively. Each of the cam wedges 646, 648, and 650 may include a camming surface that is sloped, slanted or inclined with respect to a base of the sled 600. The camming surface of each of the cam wedges 646, 648, and 650 may include one or more inclines having one or more degrees of inclination. In the embodiments illustrated in FIG. 9, each of the camming surfaces associated with the cam wedges 646, 648, and 650 includes first and second inclines 670, 672, respectively. First and second inclines 670, 672, respectively, may be configured such that the second incline 672 has a greater degree of inclination with respect to the base of the sled 600 than the first incline 670, as shown in FIG. 9. Conversely, first and second inclines 670, 672, respectively, may be configured such that the first incline 670 has a greater degree of inclination with respect to the base of the sled 600 than the second incline 672. The specific degree of inclination of each of the first and second inclines with respect to the base of the sled 600 and/or each other will depend on the contemplated uses of a manufacturer. Inner cam wedges 646 have proximal ends 652 that are relatively rigid as compared to middle and/or outer cam wedge 648 and 650, respectively, which have proximal ends 654, 656, or portions thereof that are flexible, deflectable, or collapsible. The outermost cam wedge (i.e., 650) is the most flexible. Respective proximal ends 654, 656 of middle and outer cam wedges 648, 650 each define a respective gap distance "$G_1$", "$G_2$". Gap distances "$G_1$", "$G_2$" separate respective top or deflectable portions 658, 660 of middle and outer cam wedges 648, 650 (FIG. 9). Deflectable portions 658, 660, are configured to deflect in a direction "D" (FIG. 9) toward a base of the sled 600 when the surgical fastener 130 contacts surgical fastener forming depression 91 of anvil late 90, as best seen in FIG. 5B. Deflectable portions 658, 660 are configured to contact a respective bottom or non-deflectable portion 662, 664. Gap distances "$G_1$", "$G_2$" control how much or how little deflectable portions 658, 660 deflect. That is, a greater gap distance enables deflectable member 652 to deflect to a greater extent and a lesser gap distance enables deflectable member 652 to deflect to a lesser extent. Alternatively, or in addition thereto, the proximal ends 654, 656 can have a void or a notched area that, alone or in conjunction with a gap, can alter the amount of deflection of deflectable members 658, 660. This of course will depend on contemplated uses of a manufacturer. While sled 600 is shown having inner, middle, and outer cam wedges 646, 648, and 650 respectively, it is within the purview of the present disclosure to have more or less cam wedges.

Those skilled in the art will appreciate that several variations of the above described sled configurations may be employed to achieve the same or similar result. For example, instead of having middle and outer cam wedges 648, 650 that employ a notched area, middle and/or outer cam wedges 648, 650, may simply be made from material that is configured to flex or "give" when surgical fastener 130 contacts the anvil pockets 90. Here, the flexibility of middle and/or outer cam wedges 648. 650 will provide the required deflection.

As noted, the cam wedges 644 closer to central support 645 (e.g., cam wedges 646), and thus closest to the cut-line or channel 122, are relatively rigid and as a result are intended not to deflect. In operation, when cam wedges 644 contact and drive pushers 150, the corresponding surgical fasteners 130 forms a tight "B" shape when it is urged against the anvil plate 90, thereby restricting the flow of blood through the tissue surrounding the surgical fastener 130 and facilitating hemostasis. As also noted, the cam wedges 644 further from the central support 645 (e.g., cam wedges 648 and 650), and thus further from the cut-line or channel 122, are somewhat flexible and as a result are intended to deflect. In operation, when cam wedges 648, 650 contact and drive pushers 150, the driving forces and deflectability of portions 658, 660 are selected such that the corresponding surgical fasteners 130 form a less tight "B shape when the surgical fastener 130 is urged against the anvil, thereby allowing some blood to flow through the tissue surrounding the surgical fastener 130 and facilitating healing.

Figure 10:
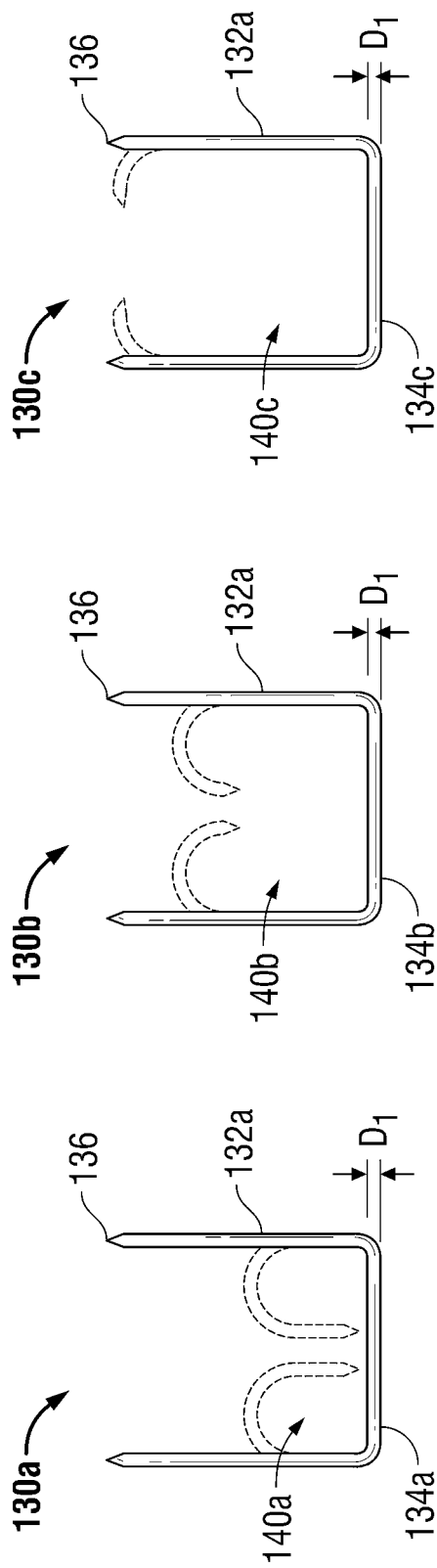
FIGS. 10A-10C illustrate the surgical fastener depicted in FIG. 6A being shown prior to and subsequent to formation (in phantom)

With reference to FIGS. 10A-10C formation of surgical fastener 130 will be described in terms of surgical fasteners $130_A$, $130_B$ and $130_C$ and their respective pushers $150_A$, $150_B$ and $150_C$, which are driven by cam wedges 646, 648, and 650 respectively. Surgical fasteners $130_A$, $130_B$, $130_C$, are substantially similar to each other. The overall heights of the surgical fasteners $130_A$, $130_B$, $130_C$, in the unformed condition (measured from the penetrating tip of the legs to the outermost surface of the backspan) are shown as being substantially equal. Surgical fasteners $130_A$, $130_B$, and $130_C$ are respectively shown in their initial and formed conditions (in phantom). In the following description, cam wedges 646 of sled 600 are configured to provide the driving force for surgical fasteners $130_A$ and cam wedges 648 and 650 having respective gap distances "$G_1$" and "$G_2$" are configured to provide the driving force for surgical fasteners $130_B$ and $130_C$. The respective dimensions of gap distances "$G_1$", "$G_2$", of surgical cam wedges 648, 650, are selected, which, in turn, alters the dimensions of the compressive spaces $140_B$ and $140_C$ occupied by stapled tissue segments "$T_1$", "$T_2$" when the respective surgical fasteners $130_B$ and $130_C$ are in their formed conditions. As noted, the driving force required to buckle and form surgical fasteners $130_A$, $130_B$, and $130_C$, against the corresponding portion of the anvil is provided by the pusher and sled configuration operatively connected to the cartridge 100. Because middle and outer cam wedges 648 and 650, respectively, are relatively flexible and configured to "give" or deflect during formation of respective surgical fasteners $130_B$ and $130_C$, these surgical fasteners form a "B" shape with a larger tissue compression space 140. The gap distances "$G_1$", "$G_2$" may be the same or vary to effectuate formed fasteners with compressive spaces that are the same or vary. Because inner cam wedges 646 are relatively rigid and configured not to "give" or deflect during formation surgical fastener $130_A$, these surgical fasteners form a "B" shape with a smaller tissue compression space 140. By altering the respective dimensions of gap distances "$G_1$", "$G_2$", any desired level of hemostasis and blood flow in the stapled tissue segments "$T_1$", "$T_2$" may be effectuated. Other various attributes of the tissue (e.g., thickness or the presence of scar tissue) may increase or diminish the level of hemostasis and blood flow in the stapled tissue segments.

Surgical fastener $130_C$ has a diameter "$D_1$". When the surgical fastener $130_C$ is formed (phantomly shown in FIG. 10C) within tissue segments "$T_1$", "$T_2$", the backspan $134_C$ cooperates with the legs 132 of the surgical fastener $130_C$ to form tissue compressive space $140_C$ (FIG. 10C). As noted, the surgical fasteners deployed further from the cut line or channel 122 deflect a respective deflectable member more than the surgical fasteners deployed closer to the cut-line, and, as a result, provides the largest compression zone. Thus, because cam wedge 650 includes a gap distance "$G_2$" that is greater than gap distance "$G_1$" of cam wedge 648, deflectable portion 660 deflects to a greater extent than deflectable member 658 of cam wedge 648. As a result, surgical fastener $130_C$ forms a less tight "B" shape than surgical fasteners $130_A$ and $130_B$ when urged against a respective anvil portion. The resultant compression space or zone $140_C$ is larger, providing minimal blood flow restriction when the tissue segments are stapled together.

Surgical fastener $130_B$ has a diameter "$D_1$". When the surgical fastener $130_B$ is formed (phantomly shown in FIG. 10B) within tissue segments "$T_1$", "$T_2$", the backspan $134_B$ cooperates with the legs 132 of the surgical fastener $130_B$ to form tissue compression space $140_B$ (FIG. 10B). Here, because the gap distance "$G_1$" of cam wedge 648 is less than the gap distance "$G_2$" of cam wedge 650, deflectable portion 658 of cam wedge 648 deflects to a lesser extent than deflectable member 660 of cam wedge 650. As a result, surgical fastener $130_B$ forms a tighter "B" shape than surgical fastener $130_C$ when urged against a respective anvil portion. The resultant compression space $140_B$ is less than the compression space $140_C$ of fastener $130_C$ Accordingly, because the pressure exerted on the tissue segments "$T_1$", "$T_2$" by surgical fastener $130_B$ is greater than the pressure exerted on the tissue segments "$T_1$", "$T_2$" by surgical fastener $130_C$, the blood flow through the tissue surrounding surgical fastener $130_B$ will be less (more restricted) than the blood flow through the tissue surrounding surgical fastener $130_C$, thereby further facilitating hemostasis. However, because blood flow is not completely restricted through tissue compression space $140_B$, unnecessary necrosis of the stapled tissue may be prevented and/or impeded.

Surgical fastener $130_A$ has a diameter "$D_1$". When the surgical fastener $130_A$ is formed (phantomly shown in FIG. 10A) within tissue segments "$T_1$", "$T_2$", the backspan $134_A$ cooperates with the legs 132 of the surgical fastener $130_A$ to form tissue compression space $140_A$ (FIG. 10A). Here, because the cam wedge 646 of sled 600 is relatively rigid and configured not to deflect, the resultant compression space $140_A$ is less than the compression space $140_B$ of fastener $130_B$. Accordingly, because the pressure exerted on the tissue segments "$T_1$", "$T_2$" by surgical fastener $130_A$ is greater than the pressure exerted on the tissue segments "$T_1$", "$T_2$" by surgical fasteners $130_B$, $130_C$, the blood flow through the tissue surrounding surgical fastener $130_A$ will be less (more restricted) than the blood flow through the tissue surrounding surgical fasteners $130_B$, $130_C$, thereby further facilitating hemostasis. Because blood flow is substantially, if not completely restricted through tissue compression space $140_A$, this results in facilitating and effectuating hemostasis.

FIG. 11 illustrates the surgical fasteners $130_A$, $130_B$, and $130_C$ and their respective pushers $150_A$, $150_B$, and $150_C$ loaded within the cartridge body 112 shown in FIGS. 1 and 4. The surgical fasteners $130_A$, $130_B$, and $130_C$, and their respective pushers, are arranged to define a pair of inner, middle, and outer rows $128_A$, $128_B$, and $128_C$, respectively, of fastener retention slots 126 formed in the top wall 120 of cartridge 100. The pair of inner, middle, and outer rows $128_A$, $128_B$, and $128_C$, respectively, are each spaced laterally from the channel 122, on opposite sides thereof, such that the surgical fasteners $130_A$, $130_B$, and $130_C$ will be deployed on opposite sides of the cut-line or channel 122 created in the tissue upon fastening. That is, the fasteners $130_A$, which are driven by cam wedges 646 that are relatively rigid and configured not to deflect, provide a greater compressive force as there is a shorter distance between the inner surface of the backspan and the curve of the formed legs, and in the illustrated embodiment are provided in the inner rows closer to the cut line. The fasteners $130_B$, which are driven by cam wedges 648 that are relatively flexible and configured to deflect, have a greater distance between the curve of the legs and the inner surface of the backspan and are provided on the outer rows where the tissue might be thicker as a result of clamping by the instrument jaws (anvil and cartridge). If a third row of fasteners $130_C$ is used in this embodiment, then the fasteners of FIG. 10C, which are driven by cam wedges 650 that are flexible and configured to deflect to the greatest extent (largest compression space), would preferably be placed on the outermost row furthest from the cut line. It should be appreciated, however, that the fasteners can be placed on other rows than the foregoing.

In one particular embodiment, the outer rows $128_C$, intermediate rows $128_B$, and inner rows $128_A$ are comprised solely of surgical fasteners $130_C$, $130_B$, and $130_A$, respectively such that the flow of blood through the tissue immediately surrounding the cut-line or channel is substantially, if not completely, restricted by the inner row $128_A$ of surgical fasteners $130_A$, whereas the flow of blood through the tissue surrounding the intermediate and outer rows $128_B$, $128_C$ is less restricted by surgical fasteners $130_B$, $130_C$, respectively.

Accordingly, the flow of blood is minimized in the tissue immediately adjacent the cut-line and is increased gradually as the lateral distance from the cut-line is also increased. It should be appreciated that the diameters of the fasteners could be varied to accommodate tissue of different thicknesses and to control tissue compression by the fasteners. In addition, the formed configuration of the fasteners can be varied to vary the tissue compression applied by the fasteners. For example, the backspan of fastener $130_A$ may be dimpled or crimped to decrease the compression space of the formed fastener.

As discussed above in connection with FIGS. 10A, 10B and 10C, the overall heights of the surgical fasteners $130_A$, $130_B$, $130_C$, in the unformed condition are substantially equal. In other embodiments, the heights of the surgical fasteners can be different in one row, as compared to another row in the cartridge, to correspond to the desired shape of the completed formed surgical fastener and/or complement the configuration of the wedges on the sled. In addition, the heights of the surgical fasteners can be different for one location in the cartridge, as compared to another location in the cartridge From the foregoing and with reference to the various figure drawings, those skilled in the art will appreciate that certain modifications can also be made to the present disclosure without departing from the scope of the same. For example, the surgical fasteners described herein above may be formed from a variety of surgically acceptable materials including various metals and absorbable and non-absorbable plastics. Additionally, any of the aforementioned surgical fasteners may be treated, chemically or otherwise, prior to being loaded into cartridge 100.

It is also contemplated that the backspan 134 of the surgical fastener 130 may include one or more pockets (not explicitly shown) that are positioned to engage the legs 132 during formation of the surgical fastener 130 and configured to redirect the legs 132 such that they are coiled toward the backspan 134, as discussed in commonly owned U.S. patent application Ser. No. 11/444,664, filed Jun. 1, 2006, the entire contents of which are incorporated by reference herein.

Figures 7A, 7B:
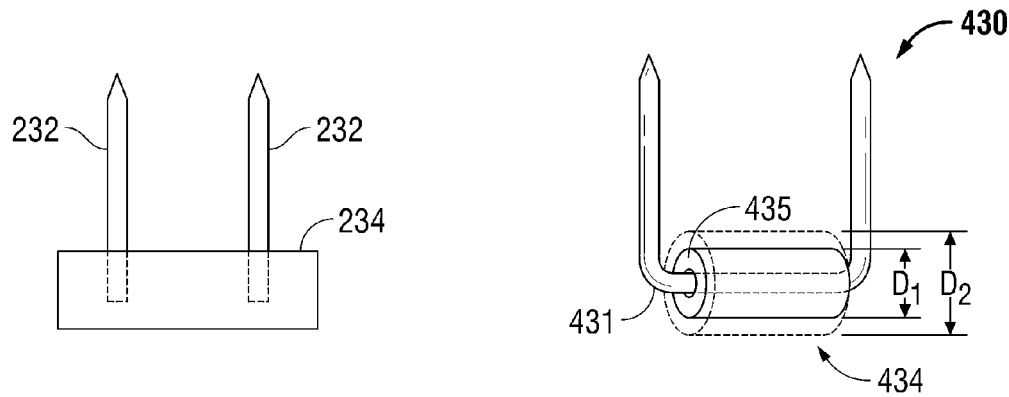
FIGS. 7A-7D illustrate alternate embodiments of surgical fasteners according to the present disclosure.
Figures 7C, 7D:
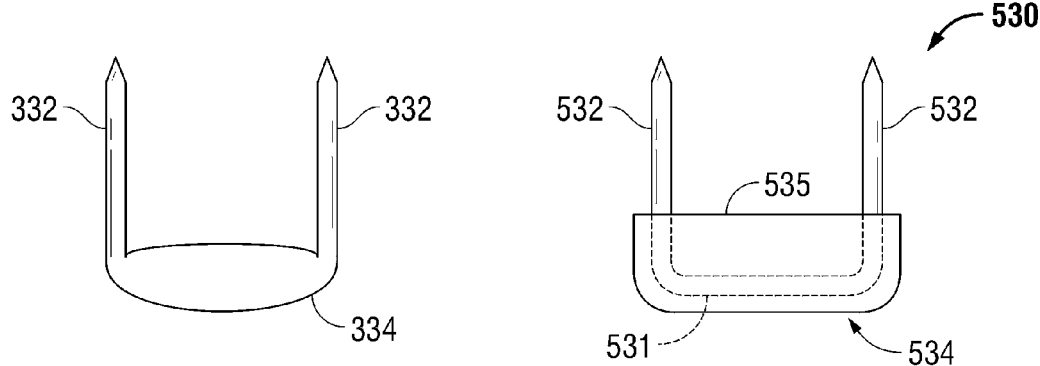

It is contemplated that in addition to varying the gap distances "G" of the cam wedges 644, the thickness of the backspan 134 and the legs 132 may also be varied such that the surgical fastener 130 closer to the cut line provides a greater compression force to stapled tissue occupied therein than the surgical fastener 130 further from the cut line. For example, in the embodiment of FIGS. 6 and 8, the backspan and legs are shown having a uniform diameter. It should be appreciated that the diameter of the legs and backspan, or portions thereof, can vary within the fastener. Examples of varying size backspan are shown in FIGS. 7A-7B. In the embodiment of FIG. 7A, the backspan is enlarged with respect to the legs and is an integral element 234 in which the fastener legs 232 are embedded. In FIG. 7C, the backspan is 334 is integral with the fastener legs 332. In the embodiments of FIGS. 7B and 7D, a separate backspan material is attached to the fastener 430, 530, respectively, with backspan 434 of FIG. 7B including a cylindrical collar 435 encircling the backspan portion 431 of the fastener 430 and the backspan 534 of fastener 530 of FIG. 7D encompassing the backspan portion 531 of the fastener and a portion of the fastener legs 532. The backspan material of FIGS. 7B and 7D can be composed of any suitable material, by way of example. Varying the thickness or height of these backspans or backspan materials can vary the compression force of the formed staple by varying the distance between the curved legs and inner portion of the backspan. This variation can be provided in addition to the varying gap distances of the cam wedges to accommodate varying tissue thicknesses. FIG. 7B illustrates this varying backspan by showing in phantom a collar of larger diameter (D2 compared to D1) to decrease the compression area. Other backspan shapes and attachments to achieve the various compression forces are also contemplated.

Additionally, while the inner, middle, and outer rows $128_A$, $128_B$, and $128_C$, respectively, are shown as including the surgical fasteners $130_A$, $130_B$, $130_C$, respectively, the present disclosure contemplates the inclusion of the surgical fasteners $130_A$, $130_B$, and $130_C$, in other rows or arrangement of any of the surgical fasteners $130_A$, $130_B$, and $130_C$, disclosed herein, either exclusively, such that only a single type of surgical fastener, e.g., surgical fastener 130, is present in a particular row, or in combination, such that a variety of surgical fasteners, e.g., surgical fasteners $130_A$, $130_B$, and $130_C$, are present. Here, one or more of the above-referenced surgical fasteners, such as, for example, those surgical fasteners depicted in FIGS. 7A-7D, may be employed, and as noted, may have varying thickness to facilitate effectuating any desired level of hemostasis and blood flow in the stapled tissue segments "$T_1$", "$T_2$".

The surgical fastener applying apparatus according to certain embodiments of the present disclosure includes a plurality of cam bars for interacting with the pushers to deploy the surgical fasteners. For example, the apparatus disclosed in U.S. Pat. No. 5,318,221, the disclosure of which is hereby incorporated by reference herein, in its entirety, has a cam bar adapter that holds a plurality of cam bars and a knife. A channel is advanced through operation of the handle of the apparatus, which drives the cam bars and knife forward. A clamp tube that surrounds the proximal end of the anvil is advanced to clamp the anvil and cartridge together. In another example, the apparatus disclosed in U.S. Pat. No. 5,782,396, the disclosure of which is hereby incorporated by reference herein, in its entirety, has an actuation sled. An elongated drive beam is advanced distally through operation of the handle of the apparatus, driving the actuation sled forward. The distal end of the drive beam engages the anvil and the channel that supports the cartridge as the drive beam travels distally, to deploy the staples and clamp the anvil and cartridge together. The surgical fastener applying apparatus shown in U.S. Pat. No. 7,070,083 employs a pusher bar incorporating a plurality of pushers that are advanced substantially simultaneously to deploy the fasteners against an anvil. One or more of the pushers may incorporate a deflectable portion, in certain embodiments of the present disclosure.

Figure 12:
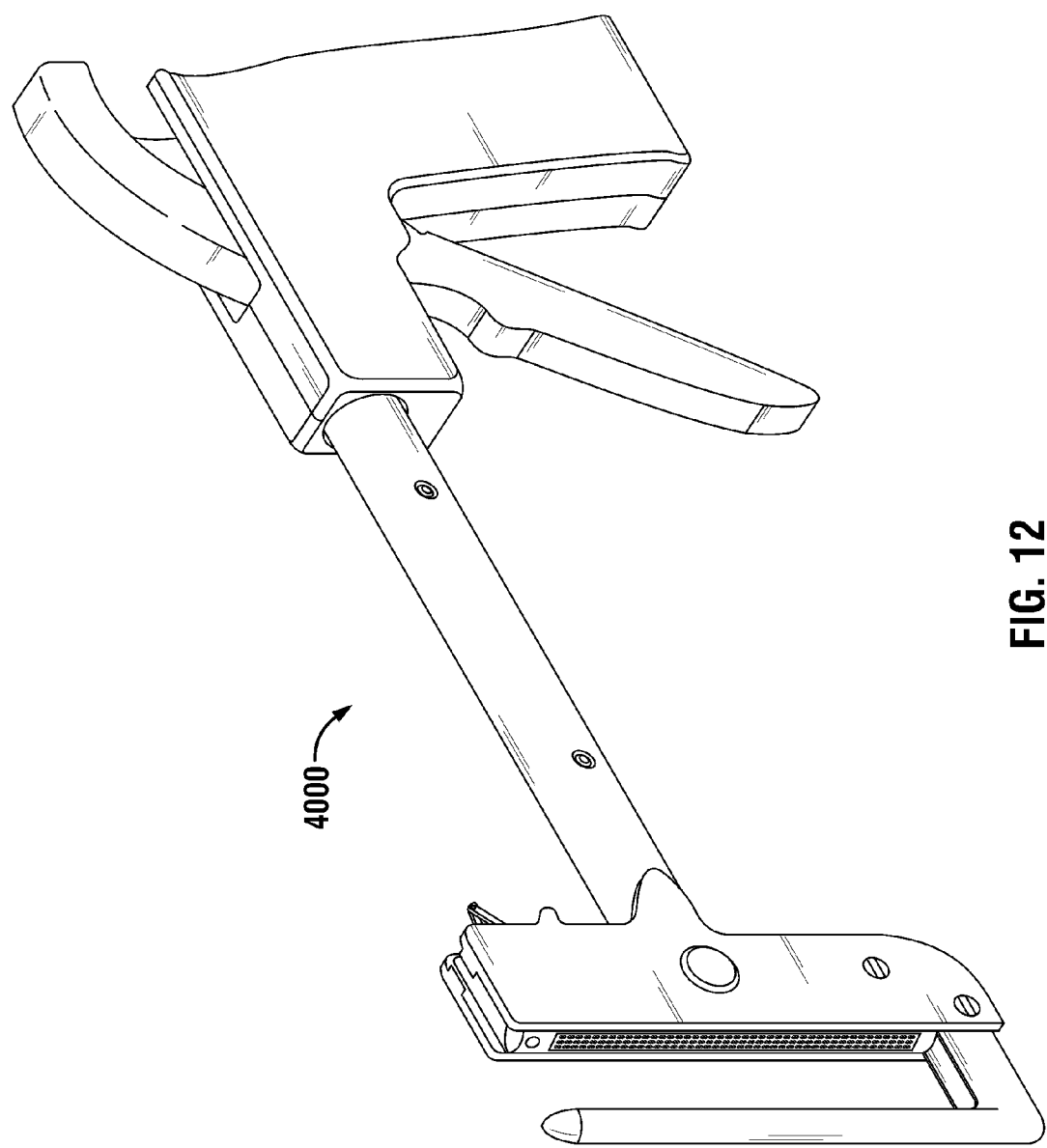
FIG. 12 illustrates another type of surgical fastener device that may employ an alternate embodiment of surgical fastener cartridge in accordance with the present disclosure.

The surgical fastening cartridge 100 may also be employed with a surgical fastener applying apparatus 4000 (FIG. 12) that is used to simultaneously deploy a plurality of surgical fasteners (surgical fasteners 130 for example) into either side of a target section of tissue (not explicitly shown). Here, a scalpel or other such cutting element may be used to remove the target section of tissue. Further details regarding the use and function of surgical fastener applying apparatus 4000 may be obtained through reference to U.S. Pat. No. 7,070,083 the entire contents of which having been previously incorporated by reference herein. In an alternate embodiment, the apparatus 4000 could include a cutting element as in the other cartridges disclosed herein.

It is contemplated that an actuation sled for a surgical stapling apparatus comprises at least one cam wedge having an angled cam surface arranged for interacting with a staple pusher supporting a surgical staple, the at least one cam wedge having a deflectable portion configured to deflect in response to a driving force exerted on the actuation sled for forming the surgical staple against an anvil. It is also contemplated that an actuation sled for a surgical stapling apparatus comprises a first cam wedge having a first angled cam surface arranged for interacting with a first staple pusher supporting a first surgical staple, and a second cam wedge having a second angled cam surface arranged for interacting with a second staple pusher supporting a second surgical staple, the first cam wedge having a deflectable portion having a first deflection in response to a driving force exerted on the actuation sled for forming the first surgical staple against an anvil. In certain embodiments, the second cam wedge has a deflectable portion having a second deflection in response to the driving force exerted on the actuation sled for forming the second surgical staple against the anvil. Alternatively, the second cam wedge may be substantially non-deflectable.

A surgical stapling apparatus having a staple cartridge is contemplated, the apparatus including an actuation sled with a first cam wedge having an angled cam surface arranged for interacting with a first staple pusher supporting a first surgical staple, and a second cam wedge having an angled cam surface arranged for interacting with a second staple pusher supporting a second surgical staple, the staple cartridge defining a channel for accommodating the passage of a knife blade, the first cam wedge being disposed adjacent the channel an in-between the channel and the second cam wedge, the second cam wedge having a deflectable portion configured to deflect in response to a driving force exerted on the actuation sled for forming the second surgical staple against an anvil.

Although the illustrative embodiments of the present disclosure have been described herein with reference to the accompanying drawings, the above description, disclosure, and figures should not be construed as limiting, but merely as exemplary of various embodiments.

What is claimed is:

1. A surgical fastener cartridge comprising:
   a cartridge body including a tissue contacting surface, the tissue contacting surface including a plurality of fastener retention slots;
   a plurality of surgical fasteners operatively disposed in the plurality of fastener retention slots;
   a plurality of pushers operably associated with the plurality of surgical fasteners, each pusher of the plurality of pushers configured for ejecting an associated surgical fastener of the plurality of surgical fasteners towards a depression in an anvil; and
   an actuation sled housed within the cartridge body, the actuation sled includes a plurality of cam wedges, including a first cam wedge and a second cam wedge, the first cam wedge having a first camming surface, a first base, and a deflectable portion, the first camming surface configured to contact at least one pusher of the plurality of pushers, the first base configured to move along a portion of the cartridge body, the first camming surface deflectable towards the first base, the second cam wedge having a second camming surface and a second base, the second camming surface being fixed from movement with respect to the second base, the actuation sled configured to sequentially contact the plurality of pushers such that the plurality of surgical fasteners is ejected from the plurality of fastener retention slots.

2. The surgical fastener cartridge according to claim 1, wherein the actuation sled is adapted to operatively connect to a drive assembly associated with a surgical fastening apparatus such that the actuation sled is longitudinally movable within the cartridge body.

3. The surgical fastener cartridge according to claim 1, wherein the tissue contacting surface includes a channel configured to accommodate longitudinal movement of a cutting element.

4. The surgical fastener cartridge according to claim 3, wherein a central support of the actuation sled is configured to engage an abutment surface of the cutting element.

5. The surgical fastener cartridge according to claim 1, wherein the actuation sled has a central support.

6. The surgical fastener cartridge according to claim 5, wherein the second cam wedge is closer to the central support than the first cam wedge.

7. The surgical fastener cartridge according to claim 1, wherein the second cam wedge includes a proximal end that is more rigid than a proximal end of the first cam wedge.

8. The surgical fastener cartridge according to claim 7, wherein the proximal end of the first cam wedge includes a notched area configured to alter an amount of deflection of the first cam wedge.

9. The surgical fastener cartridge according to claim 1, wherein a proximal end of the first cam wedge includes a notched area configured to allow deflection of the first camming surface toward the first base during the formation of the plurality of surgical fasteners.

10. The surgical fastener cartridge according to claim 1, wherein a proximal end of the actuation sled is configured for selective engagement with an axial drive assembly.

11. The surgical fastener cartridge according to claim 1, wherein the camming surface of the first cam wedge is deflectable towards the base of the first cam wedge a first distance, the actuation sled includes a third cam wedge having a deflectable portion and a base, the camming surface of the third cam wedge is deflectable towards the base of the third cam wedge a second distance, the first distance is different from the second distance.

12. The surgical fastener cartridge according to claim 1, wherein the camming surface of the first cam wedge and the base of the first cam wedge define a gap therebetween, the gap disposed at a proximal end of the actuation sled.

13. The surgical fastener cartridge according to claim 1, wherein the actuation sled is configured for selective engagement with an axial drive assembly.

14. An actuation sled for use with a cartridge body of a surgical instrument, the actuation sled comprising:
 a first cam wedge including a camming surface and a base, the camming surface configured to contact at least one pusher to cause ejection of at least one surgical fastener from the cartridge body, the base configured to move along a portion of the cartridge body, the camming surface deflectable towards the base, the camming surface and the base defining a gap therebetween, the gap disposed at a proximal end of the actuation sled, the proximal end of the actuation sled configured for selective engagement with an axial drive assembly; and
 a second cam wedge including a camming surface and a base;
 a third cam wedge including a camming surface and a base, the camming surface of the third cam wedge is non-deflectable with respect to the base of the third cam wedge;
 wherein the camming surface of the first cam wedge is deflectable towards the base of the first cam wedge a first distance, the camming surface of the second cam wedge is deflectable towards the base of the second cam wedge a second distance, the first distance is different from the second distance.

15. The actuation sled according to claim 14, wherein the gap is configured to decrease in size when the camming surface is deflected towards the base.

* * * * *